United States Patent
Singer et al.

(10) Patent No.: US 7,060,837 B2
(45) Date of Patent: Jun. 13, 2006

(54) METHOD FOR THE PURIFICATION OF LANSOPRAZOLE

(75) Inventors: Claude Singer, Kafar Saba (IL); Anita Liberman, Tel-Aviv (IL); Irena Veinberg, Rehovot (IL); Nina Finkelstein, Herzliya (IL); Tamar Nidam, Yehud (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 27 days.

(21) Appl. No.: 11/083,652

(22) Filed: Mar. 18, 2005

(65) Prior Publication Data

US 2005/0165060 A1 Jul. 28, 2005

Related U.S. Application Data

(62) Division of application No. 10/646,059, filed on Aug. 21, 2003, now Pat. No. 6,909,004.

(60) Provisional application No. 60/418,056, filed on Oct. 11, 2002, provisional application No. 60/404,845, filed on Aug. 21, 2002.

(51) Int. Cl.
*C07D 401/12* (2006.01)

(52) U.S. Cl. .................................... 546/273.7
(58) Field of Classification Search ............... 546/273.7
See application file for complete search history.

(56) References Cited

U.S. PATENT DOCUMENTS

| 4,628,098 | A | 12/1986 | Nohara et al. |
| 4,689,333 | A | 8/1987 | Nohara et al. |
| 5,026,560 | A | 6/1991 | Makino et al. |
| 5,045,321 | A | 9/1991 | Makino et al. |
| 5,093,132 | A | 3/1992 | Makino et al. |
| 5,433,959 | A | 7/1995 | Makino et al. |
| 5,578,732 | A | 11/1996 | Kato et al. |
| 6,002,011 | A | 12/1999 | Kato et al. |
| 6,166,213 | A | 12/2000 | Anousis et al. |
| 6,180,652 | B1 | 1/2001 | Tsujii et al. |
| 6,268,502 | B1 | 7/2001 | Milac et al. |
| 6,313,303 | B1 | 11/2001 | Tagami et al. |

FOREIGN PATENT DOCUMENTS

| ES | 2 063 705 | 1/1995 |
| ES | 2 105 953 | 10/1997 |
| WO | WO 99/47514 | 9/1999 |
| WO | WO 01/21617 A1 | 3/2001 |
| WO | WO 01/68594 A1 | 9/2001 |

OTHER PUBLICATIONS

The United States Pharmacopeial Convention, Inc., Pharmacopeial Forum vol. 26 No. 5., pp. 1229-1232.; 2000.
Drug Development and Industrial Pharmacy Stabilization of a New Antiulcer Drug (Lansoprazole) in the Solid Dosage Forms, pp. 1437-1447, 1992.

*Primary Examiner*—Patricia L. Morris
(74) *Attorney, Agent, or Firm*—Kenyon & Kenyon LLP

(57) ABSTRACT

The present invention provides a method for preparing a substantially pure lansoprazole containing less than about 0.2% (wt/wt) impurities including sulfone/sulfide derivatives. The present invention also provides a process for recrystallizing lansoprazole to obtain a lansoprazole containing less than about 0.1% (wt/wt) water.

16 Claims, No Drawings

METHOD FOR THE PURIFICATION OF LANSOPRAZOLE

CROSS-REFERENCE TO RELATED APPLICATIONS

This application is a divisional of U.S. patent application Ser. No. 10/646,059, filed Aug. 21, 2003 now U.S. Pat. No. 6,909,004, which claims the benefit of the U.S. Provisional Application Ser. Nos. 60/404,845 filed Aug. 21, 2002 and 60/418,056 filed Oct. 11, 2002, the disclosures of which are incorporated by reference in their entirety herein.

FIELD OF THE INVENTION

The present invention relates to a method for preparing a substantially pure 2-(2-pyridylmethyl)sulfinyl-1H-benzimidazole (lansoprazole) that is free of sulfone and sulfide derivatives. The present invention also relates to a method of preparing a lansoprazole containing <0.1% (wt/wt) water.

BACKGROUND OF THE INVENTION

Several substituted 2-(2-pyridylmethyl)sulfinyl-1H-benzimidazole derivatives are well-known gastric proton pump inhibitors. These benzimidazole derivatives include lansoprazole, omeprazole, pantoprazole, and rabeprazole. This class of benzimidazole derivatives is generally represented by the following chemical formula A:

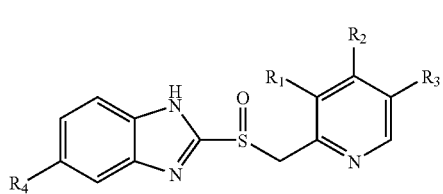

U.S. Pat. No. 4,628,098 describes the generic lansoprazole compound. Lansoprazole has as its chemical name (2-[[[3-methyl-4-(2,2,2-trifluoro-ethoxy)-2-pyridinyl]methyl]sulfinyl]-1H-benzimidazole), i.e., when $R_1$ is methyl, $R_2$ is trifluoro-ethoxy, $R_3$ is hydrogen and $R_4$ is hydrogen.

As a characteristic shared with other benzimidazole derivatives (e.g., ompeprazole and pantoprazole), lansoprazole can inhibit gastric acid secretion, and thus commonly used as an antiulcer agent.

Several methods for preparing lansoprazole are known. The majority of these methods involve the use of a lansoprazole precursor that contains a thioether group. The thioether group is oxidized in the last step of preparation to form the lansoprazole.

U.S. Pat. Nos. 4,628,098 and 5,578,732 (the '732 patent) describe the oxidation of the thioether group using m-chloro-perbenzoic acid as the oxidizing agent. However, the use of m-chloro-perbenzoic acid often results in a non-selective oxidation of the thioether group. The '732 patent further describes an oxidation method with hydrogen peroxide ($H_2O_2$) in the presence of a specific vanadium catalyst. Other patents such as ES 2105953, WO 0121617, ES 2063705, U.S. Pat. No. 6,313,303, WO9947514, WO0168594 describe the use of other oxidation reagents and/or other catalysts. None of these oxidation methods result in selective oxidation of the thioether group.

In addition, the preparation of lansoprazole by conventional methods is always accompanied by the formation of small quantities of the corresponding sulfone derivative as an impurity. For example, U.S. Pat. No. 6,180,652 (the '652 patent) describes the presence of sulfone derivative. Formation of sulfone derivative brings about the drawback of low yield of the desired sulfoxide.

Although attempts have been made to separate the sulfone derivative from lansoprazole, it is not a simple task, given their very similar structures and physicochemical properties. For this purpose, the '652 patent describes a method which permits separation of lansprazole from its sulfone derivative. An acetone complex of the lansoprazole salt is purified in this method.

Lansoprazole and other 2-(2-pyridylmethyl)sulfinyl-benzimidazole derivatives tend to lose stability and undergo decomposition when contaminated with traces of a solvent, particularly water, in their crystal structure. It is desirable that the benzimidazole crystals be solvent free (i.e., residual solvent should be reduced to a minimum).

The '732 patent describes the crystallization of lansoprazole using a ethanol:water solvent system (vol:vol of ethanol:water is 9:1). U.S. Pat. No. 6,002,011 (the '011 patent) describes the crystallization of lansoprazole from the same ethanol:water system, containing traces of ammonia (0.03 mole $NH_4OH$: 1 mole lansoprazole). The '011 patent discloses a reslurry method in water, which permits to obtain more stable "solvent free" lansoprazole. The '011 patent fails to disclose the level of purity for lansoprazole. In addition, the ethanol and water are difficult to eliminate. Even after intensive drying, lansoprazole still contains solvent and is unstable under storage.

There is continuing need to obtain 2-(2-pyridylmethyl)sulfinyl-1H-benzimidazoles (e.g., lansoprazole) that are free of contaminants including sulfone and sulfide derivatives. There has also been a long-felt need for a method to prepare 2-(2-pyridylmethyl)sulfinyl-1H-benzimidazoles (e.g., lansoprazole) having reduced water content (<0.1% wt/wt water).

We discovered that "solvent free" lansoprazole can be obtained by the crystallization from different solvents. Lansoprazole obtained by this method of crystallization can be dried to <0.1% water, as is required by the USP forum.

SUMMARY OF THE INVENTION

In one aspect, the present invention provides a method of purifying lansoprazole, especially to 0.20% impurites or less, which method includes the steps of: providing a solution of lansoprazole in a solvent selected from an organic solvent, especially an alcohol (especially ethanol), acetone, 2-butanone, dimethyl-formamide and tetrahydrofuran, or a mixture of organic solvent and water in the presence of an amine compound, especially ammonia, ammonium hydroxide, diethyl amine, triethyl amine, or methyl amine, especially in equimolar ratio (or higher) to the lansoprazole; combining the provided solution with an acid, especially acetic acid, formic acid, or hydrochloric acid; and isolating the purified lansoprazole. When the solvent is a mixture of organic solvent and water, the ratio of organic solvent to water is especially about 0.2:1 to about 3:1 and the volume-to-weight ratio of such solvent to lansoprazole is about 17:1 to about 5:1, especially about 11:1.

In another aspect, the present invention relates to a method of preparing a lansoprazole containing less than about 0.1% (wt/wt) water (i.e. for desolvation lansoprazole) comprising the steps of: crystallizing, optionally in the presence of an amine compound in a mole ratio of about 0.05:1 relative to lansoprazole, especially at 50° C. or less, a lansoprazole (which can be wet or dry) from solution in a solvent that is an organic solvent, especially acetone, 2-butanone, methanol, dimethyl-carbonate, and diethyl-carbonate, or a mixture of an organic solvent and water; and isolating the lansoprazole containing less than about 0.1% (wt/wt) water. Crystallization can be effected by lowering the temperature of the solution, combining the soloution with water (less than about 20% vol/vol), or both.

In still a further aspect, the present invention relates to a method of purifying lansoprazole to obtain lansoprazole having less than about 0.1%, wt/wt, water comprising the steps of: providing a solution of lansoprazole in a solvent selected from an organic solvent, especially ethanol, or a mixture of organic solvent and water in the presence of an amine compound, wherein the amine compound is present at a ratio of about 1:1, mole:mole, relative to lansoprazole; combining the provided solution with an acid, especially acetic acid, formic acid, or hydrochloric acid; isolating the lansoprazole; dissolving the isolated lansoprazole in an organic solvent selected from the group consisting of acetone, 2-butanone, methanol, dimethyl-carbonate, and diethyl-carbonate (especially acetone), optionally in the presence of an amine compound; and isolating the purified lansoprazole having less than about 0.1%, wt/wt, water.

In yet another aspect, the present invention relates to lansoprazole having less than 0.20 wt-% impurities, especially when the water content is 0.1% by wt or less.

In a further aspect, the present invention relates to lansoprazole having less than 0.20 wt-% combined sulfide and sulfone derivatives, especially when the water content is 0.1 wt-% or less.

In still a further aspect, the present invention relates to lansoprazole having less than 0.10% wt-% of either sulfone or sulfide derivative, especially in combination with a water content of 0.1 wt-% or less.

DETAILED DESCRIPTION OF THE INVENTION

As used herein "LNPS" refers to the sulfide-containing starting compound for lansoprazole preparation. The chemical name for LNPS is 2-[[3-methyl-4-(2,2,2-trifluoroethoxy)-2-pyridinyl]thio]-1H benzimidazole. "LNP" refers to lansoprazole which has the chemical name of 2-[[3-methyl-4-(2,2,2-trifluoroethoxy)-2-pyridinyl]methyl]sulfinyl-1H benzimidazole. The present invention provides a "substantially pure" lansoprazole. Substantially pure lansoprazole contains less than about 0.10% (wt/wt) sulfone derivative and less than about 0.10% sulfide derivative. Water is not considered an imputity per se, but its presence in lansoprazole is undesirable. The present invention also provides lansoprazole that contains less than about 0.1% (wt/wt) water, referred to as "solvent free" (i.e. desolvated) lansoprazole.

Unless otherwise stated, % and % (wt/wt) refer to percent on a weight basis.

As used herein in connection with a numerical quantity, "<" refers to less than.

In accordance with the present invention, 2-[[3-methyl-4-(2,2,2-trifluoro ethoxy)-2-pyridinyl]thio]-1H benzimidazole (LNPS) is used as a starting material for preparation of 2-[[3-methyl-4-(2,2,2-trifluoroethoxy)-2-pyridinyl]methyl]sulfinyl-1H benzimidazole and is dissolved in an organic solvent or a mixture of organic solvent with water. Any residue of the LNPS remaining in the final product is an impurity and difficult to remove.

Exemplary organic solvents suitable for use in the practice of the present invention include alcohols such as ethanol, methanol, n-propanol, i-propanol; ketones such as acetone and 2-butanone; dimethyl-formamide; tetrahydrofuran; and the like. Preferably, the organic solvent is ethanol.

In particular embodiments, mixtures of an organinc solvent listed above with water can be used. When mixtures of organic solvent and water are used, different volume ratios (vol/vol) of organic solvent and water can be used. The organic solvent/water ratio can vary between about 0.2:1 to 3:1. Preferably, the solvent/water ratio is about 1.5:1. Use of larger solvent/water ratios may result in poor crystallization yields.

When mixtures of an organic solvent and water are used, the overall ratio, on a volume per weight basis, of solvent/water (i.e., organic solvent+water) to lansoprazole can vary between about 17:1 to about 5:1 (vol:wt). Preferably, the ratio of solvent/water to lansoprazole is about 11:1 (vol/wt).

Amine compounds are used in the practice of the present invention. The overall ratio, on a mole basis, of amine compound to lansoprazole (mol/mol) can vary between about 17:1 to about 1:1. Preferably, the amine compound to lansoprazole (mol/mol) ratio is about 7:1. Exemplary amine compounds useful in the practice of the present invention include ammonia, ammonium hydroxide, diethylamine, triethylamine, methylamine and the like. Preferably, the amine compound is ammonium hydroxide.

Preferably, ammonium hydroxide is present at a mol/mol ratio to lansoprazole of about 1:1 to about 7:1. Crystallization of lansoprazole under such conditions permits a good separation of lansoprazole from impurities, especially sulfone and/or sulfide derivatives.

In one embodiment, the present invention provides a crystallization purification method for purifying lansoprazole. Crystallization of lansoprazole from solution in an organic solvent or a mixture of organic solvent and water in the presence of an amine compound according to the crystallization purification method of the present invention results in substantially pure lansoprazole.

In the present invention, purification of lansoprazole by crystallization is achieved by acidifying (i.e. combining with acid) a solution of lansoprazole in an organic solvent or a mixture of organic solvent and water. The acid combined can neutralize the amine compound during the crystallization of lansoprazole.

Exemplary acids combined to crystallize lansoprazole include acetic acid, formic acid, hydrochloric acid (HCl) and the like. Preferably, the acid is acetic acid.

Although the purified lansoprazole obtained by the above-mentioned crystallization purification process is substantially pure and can be advantageous, it does not necessarily contain <0.1% water in accordance with the USP forum. As mentioned previously, water can have a negative impact on the long-term stability of lansoprazole (U.S. Pat. No. 6,002,011).

Thus, in another embodiment of the present invention, a method for reducing the water in (i.e. desolvating) lansoprazole is provided. In this embodiment, the water content of lansoprazole, especially substantially pure lansoprazole, can be reduced to <0.1% water by crystallization from organic solvent.

Exemplary crystallizing organic solvents for obtaining lansoprazole having <1%, wt/wt, water include methanol, dimethyl-carbonate, diethyl-carbonate, acetone, 2-butanone and the like. Preferably, such crystallizing organic solvents are methanol, dimethyl-carbonate and diethyl-carbonate. Most preferably, such crystallizing organic solvent is acetone.

Crystallization of lansoprazole to obtain lansopraolze having <0.1% water can be and preferably is carried-out in the presence of an amine compound. Exemplary amine compounds include ammonia, ammonium hydroxide, diethylamine, triethylamine, methylamine and the like. Preferably, the amine compound is ammonium hydroxide.

Preferably, in this embodiment, the mole ratio of amine compound to lansopraozle (mole:mole or mole/mole) is about 0.05:1.

Preferably the lansoprazole to be desolvated is completely dissolved in the solvent before crystallization. The dissolution of lansoprazole can be promoted by the presence of small amounts of water. The presence of a small amout of water can be insured by using wet lansoprazole from the previously mentioned purification step or by adding <20% (vol/vol) water to the solvent.

The dissolution of lansoprazole to be desolvated can be performed at the crystallization solvent reflux temperature. Preferred dissolution temperatures are lower than the reflux temperature, given the reported instability of lansoprazole at higher temperatures. Preferably, the dissolution temperature does not exceed 50° C.

The crystallization yield of lansoprazole can be improved by cooling or by removing solvent or water from the crystallization system. One skilled in the art would appreciate the techniques used to remove water from a mixture of organic solvent and water include, e.g., azeotropic distillation.

The present invention can be illustrated by the following nonlimiting examples.

EXAMPLE 1

Preparation of Lansoprazole Crude

Into a flask 1L ethanol was charged and cooled under stirring to 5° C. Under mixing 200 grams 2-[[3-methyl-4-(2,2,2-trifluoroethoxy)-2-pyridinyl]thio]-1H benzimidazole (LNPS) and 3 grams vanadium acetyl acetonate were added. 110 grams tert-butyl-hydroperoxide solution were dropped slowly into the suspension. The suspension was maintained under mixing during 4 hours. 40 grams of $Na_2SO_3$ dissolved in 400 mL water were added. Separate solid phase by vacuum filtration and dry. 165 grams of LNP crude were obtained (yield 79%).

Sulfone 0.3%

LNPS 0.3%

Chromatographic purity method of lansoprazole monograph in USP Forum Vol. 26(5) [September–October 2000].

HPLC Condition:

| Column: | C18 |
|---|---|
| Mobile phase: | Gradient of triethylamine in water with acetonitrile |
| Flow: | 0.8 mL/min |
| Detection: | 285 nm |

This chromatographic assay has the detection sensitivity of less than 0.1% impurities in LNP.

EXAMPLE 1A

Preparation of Lansoprazole Crude

Into a flask 1L ethanol (95%) was charged and cooled under stirring to 5° C. Under mixing 200 grams 2-[[3-methyl-4-(2,2,2-trifluoroethoxy)-2-pynridinyl]thio]-1H benzimidazole (LNPS) and 3 grams vanadium acetyl acetonate were added. 110 grams tert-butyl-hydroperoxide solution were dropped slowly into the suspension. The suspension was maintained under mixing during 6 hours. 40 grams of $Na_2SO_3$ dissolved in 400 ml water were added.

1L of water (pH was about 8–8.5; the pH was adjusted by the addition of $NH_4OH$) was added to the suspension and the suspension was further mixed for 17 hours at 25° C. The suspension was cooled to 5° C. and the solid phase separated by vacuum filtration then dried. 178 grams of LNP crude were obtained (yield 85%). Sulfone 0.15%.

EXAMPLE 2

Purification of Lansoprazole

In a 0.25 L flask 67.5 mL ethanol 95%, 15 mL of ammonium hydroxide ($NH_4OH$) 24% and 45 mL water were charged and cooled under stirring to 5° C. Under mixing 10 grams lansoprazole crude were added and heated to 52° C. to dissolution. 1 gram of active carbon was added to the slightly turbid solution and maintained a short time at 49° C. The carbon was separated on a filter and the cake washed with a mixture of 14 mL ethanol and 12 mL water. The solution was cooled and lansoprazole was precipitated by the addition of 3.75 mL acetic acid. The suspension was cooled to 10° C. and filtered. The product was washed with water and ethanol and dryed. 8.7 grams of lansoprazole pure were obtained (yield: 89%). Sulfone 0.05%, LNPS under the detection limit.

The above-described procedure was applied in other examples where the solvent and/or the amine was different. The following table is illustrative for these examples:

| Example | Solvent | water yes/no | Amine | Yield % | Sulfone % | LNPS % |
|---|---|---|---|---|---|---|
| 3 | i-propanol | no | $NH_4OH$ | 52.7 | 0.03 | 0.02 |
| 4 | Ethanol | no | $NH_4OH$ | 46.5 | 0.07 | <DL[1] |
| 5 | n-propanol | yes | $NH_4OH$ | 91.5 | 0.08 | 0.04 |
| 6 | i-propanol | yes | $NH_4OH$ | 90.8 | 0.07 | <DL |
| 7 | Ethanol | yes | Triethylamine | 87.6 | 0.05 | <DL |
| 8 | i-buthanol | yes | Triethylamine | 80.7 | 0.06 | <DL |

[1] less than detection limit

EXAMPLE 9

Preparation of Lansoprazole Containing <0.1% (wt/wt) Water

In a 0.25L flask 29.8 grams wet LNP crystal and 30 mL acetone were charged. The suspension was heated to 52° C. and 150 mL acetone was dropped until a clear solution was obtained. The solution was cooled to 10° C. and concentrated until the weight of the reaction mass was 48.5 grams. The solid was separated by filtration and washed with 20 mL cold acetone. After drying 18.58 grams product were obtained (yield: 91%). Content of water according to Karl Fischer test 0.05%.

Similar to example 3, the following other examples were performed:

| Examples | Solvent | Yield % | Water % (KF[1]) |
|---|---|---|---|
| 10 | Dimethylcarbonate | 87.5 | 0.04 |
| 11 | 2-butanone | 88.5 | 0.03 |
| 12 | Methanol | 72% | 0.06 |

[1]Karl Fisher method for Water determination is the USP method as written in USP Forum Vol. 26(5) [September–October 2000].

EXAMPLE 13

Preparation of Lansoprazole Containing <0.1% (wt/wt) Water

In a 0.1 L flask 4 grams dry LNP crystals and 60 mL acetone containing 15% water were charged. The solution was maintained under mixing at 25° C. for 17 hours. The solution was concentrated to 15 grams and filtered. After drying 3.4 grams product were obtained (yield: 84.7%). Content of water according to Karl Fischer test: 0.06%.

EXAMPLE 14

Preparation of Lansoprazole Containing <0.1% (wt/wt) Water

In a 50 mL flask 11.6 mL acetone, 3.1 mL water and 0.05 mL NH$_4$OH were charged. The solution was heated to 45° C. and under mixing 5.8 grams of LNP crystal were charged. The solution was heated to 61° C. and immediately cooled to 5–10° C. After filtration and drying 5.0 grams product was obtained (yield: 87%). Content of water according to Karl Fischer test: 0.03%.

EXAMPLE 15

Lansoprazole (5.0 grams) was dissolved in 30 ml of acetone, containing 15 volume % of water, at heating at reflux. Water (30 ml) was added dropwise for 5 min to the clear solution. After cooling to room temperature the slurry was filtered, giving after drying 4.5 grams of the product (yield: 90%). Content of the water according to Karl Fischer test was 0.08%.

EXAMPLE 16

Lansoprazole (5.0 grams) was dissolved in 30 ml of acetone, containing 15 volume % of water, at heating at reflux. Water (60 ml) was added dropwise for 5 min to the clear solution. After cooling to room temperature the slurry was filtered, giving after drying 4.6 grams of the product (yield: 92%). Content of the water according to Karl Fischer test was 0.08%.

A number of embodiments of the present invention have been described. The present invention is not to be limited in scope by the specific embodiments described herein. It will be understood that various modifications may be made without departing from the spirit and scope of the invention. Various publications are cited herein, the disclosures of which are incorporated by reference in their entireties.

What is claimed is:

1. A method of purifying lansoprazole, comprising the steps of:
   a) providing a solution of lansoprazole in a solvent selected from an organic solvent or a mixture of organic solvent and water in the presence of an amine compound;
   b) combining the provided solution with an acid, and
   c) isolating the purified lansoprazole.

2. The method of claim 1 wherein the amine compound is present in 1:1, mole:mole, ratio relative to the lansoprazole.

3. The method of claim 1, wherein solution is in an organic solvent selected from the group consisting of alcohols, acetone, 2-butanone, dimethyl-formamide and tetrahydrofuran.

4. The method of claim 3, wherein the alcohol is selected from the group consisting of ethanol, methanol, n-propanol, and i-propanol.

5. The method of claim 4, wherein the alcohol is ethanol.

6. The method of claim 1, wherein the amine compound is selected from the group consisting of ammonia, ammonium hydroxide, diethylamine, triethylamine and methylamine.

7. The method of claim 6 wherein the amine compound is ammonium hydroxide.

8. The method of claim 7 wherein the ammonium hydroxide is present at a mol/mol ratio to lansoprazole of greater than 1.

9. The method of claim 1 wherein the acid combined is selected from the group consisting of acetic acid, formic acid, and hydrochloric acid.

10. The method of claim 9 wherein the acid is acetic acid.

11. The method of claim 1, wherein the solvent is a mixture of organic solvent and water wherein the ratio of organic solvent to water is about 0.2:1 to about 3:1, vol/vol.

12. The method of claim 11 wherein the ratio of organic solvent to water is about 1.5:1, vol/vol.

13. The method of claim 1, wherein the solvent of the provided solution is a mixture of organic solvent and water and is present at a vol/wt ratio to lansoprazole of about 17:1 to about 5:1.

14. The method of claim 13 wherein the mixture of organic solvent and water is present at a vol/wt ratio to lansoprazole of about 11:1.

15. The method of claim 1, wherein the amine compound is present at a mol/mol ratio to lansoprazole of about 17:1 to about 1:1.

16. The method of claim 1, wherein the amine compound is present at a mol/mol ratio to lansoprazole of about 7:1.

* * * * *

UNITED STATES PATENT AND TRADEMARK OFFICE
CERTIFICATE OF CORRECTION

PATENT NO. : 7,060,837 B2  Page 1 of 1
APPLICATION NO. : 11/083652
DATED : March 18, 2005
INVENTOR(S) : Claude Singer et al.

It is certified that error appears in the above-identified patent and that said Letters Patent is hereby corrected as shown below:

On the Title page, item (56) OTHER PUBLICATIONS, change
"Drug Development and Industrial Pharmacy Stabilization of a New Antiulcer Drug (Lansoprazole) in the Solid Dosage Forms, pp. 1437-1447, 1992." to
-- Drug Development and Industrial Pharmacy, "Stabilization of a New Antiulcer Drug (Lansoprazole) in the Solid Dosage Forms", pp. 1437-1447, 1992. --

Column 1, lines 49-50, change "...and thus commonly used as an antiulcer agent" to -- and thus is commonly used as an antiulcer agent --

Column 3, lines 50-51, change "Water is not considered an imputity per se,..." to -- Water is not considered an impurity per se,... --

Column 3, line 61, change "4-(2,2,2-trifluoro ethoxy)..." to -- 4-(2,2,2-trifluoroethoxy)... --

Column 4, lines 64-65, change "Exemplary crystallizing organic solvents for obtaining lansoprazole having <1%, wt/wt, water include methanol,..." to -- Exemplary crystallizing organic solvents for obtaining lansoprazole having <0.1%, wt/wt, water include methanol,... --

Column 6, line 7, change "...-2-pynridinyl]thio]-..." to -- ...-2-pyridinyl]thio]-... --

Signed and Sealed this

Sixteenth Day of June, 2009

JOHN DOLL
*Acting Director of the United States Patent and Trademark Office*

UNITED STATES PATENT AND TRADEMARK OFFICE
CERTIFICATE OF CORRECTION

PATENT NO.         : 7,060,837 B2                                   Page 1 of 1
APPLICATION NO. : 11/083652
DATED              : June 13, 2006
INVENTOR(S)        : Claude Singer et al.

It is certified that error appears in the above-identified patent and that said Letters Patent is hereby corrected as shown below:

On the Title page, item (56) OTHER PUBLICATIONS, change
"Drug Development and Industrial Pharmacy Stabilization of a New Antiulcer Drug (Lansoprazole) in the Solid Dosage Forms, pp. 1437-1447, 1992." to
-- Drug Development and Industrial Pharmacy, "Stabilization of a New Antiulcer Drug (Lansoprazole) in the Solid Dosage Forms", pp. 1437-1447, 1992. --

Column 1, lines 49-50, change "...and thus commonly used as an antiulcer agent" to -- and thus is commonly used as an antiulcer agent --

Column 3, lines 50-51, change "Water is not considered an imputity per se,..." to -- Water is not considered an impurity per se,... --

Column 3, line 61, change "4-(2,2,2-trifluoro ethoxy)..." to
-- 4-(2,2,2-trifluoroethoxy)... --

Column 4, lines 64-65, change "Exemplary crystallizing organic solvents for obtaining lansoprazole having <1%, wt/wt, water include methanol,..." to
-- Exemplary crystallizing organic solvents for obtaining lansoprazole having <0.1%, wt/wt, water include methanol,... --

Column 6, line 7, change "...-2-pynridinyl]thio]-..." to -- ...-2-pyridinyl]thio]-... --

This certificate supersedes the Certificate of Correction issued June 16, 2009.

Signed and Sealed this

Fourteenth Day of July, 2009

JOHN DOLL
*Acting Director of the United States Patent and Trademark Office*